United States Patent [19]
Jacobs

[11] Patent Number: 6,120,755
[45] Date of Patent: Sep. 19, 2000

[54] METHOD FOR CLEANING TEETH BY ABRASIVE ORAL IRRIGATION

[76] Inventor: Patrick Thomas Jacobs, 4718 51st St. Ct., E, Tacoma, Wash. 98443

[21] Appl. No.: 09/224,062

[22] Filed: Jan. 2, 1999

[51] Int. Cl.⁷ ...................................................... A61K 7/16
[52] U.S. Cl. ............................................. 424/49; 433/216
[58] Field of Search ................................ 424/49, 5–2, 57; 433/216

[56] References Cited

U.S. PATENT DOCUMENTS

| | | |
|---|---|---|
| 2,056,096 | 9/1936 | Etter . |
| 2,772,659 | 12/1956 | Tennis . |
| 3,578,209 | 5/1971 | Fraser . |
| 4,078,558 | 3/1978 | Woog et al. . |
| 4,159,715 | 7/1979 | Moret et al. . |
| 4,302,186 | 11/1981 | Cammack et al. . |
| 4,337,040 | 6/1982 | Cammack et al. . |
| 4,522,805 | 6/1985 | Gordon . |
| 4,721,614 | 1/1988 | Winston et al. ............................ 424/52 |
| 4,980,154 | 12/1990 | Gordon . |
| 4,989,590 | 2/1991 | Baum et al. . |
| 5,081,799 | 1/1992 | Kirschner et al. . |
| 5,083,402 | 1/1992 | Kirschner et al. . |
| 5,182,099 | 1/1993 | Jonsson et al. ............................ 424/49 |
| 5,303,672 | 4/1994 | Morris . |
| 5,403,578 | 4/1995 | Gordon . |
| 5,730,959 | 3/1998 | Prencipe et al. ............................ 424/52 |
| 5,843,409 | 12/1998 | Campbell et al. ......................... 424/52 |
| 5,849,267 | 12/1998 | Collines et al. ........................... 424/49 |

FOREIGN PATENT DOCUMENTS

PCT/US90/
04230  of 0000  WIPO .

*Primary Examiner*—Ralph Gitomer
*Attorney, Agent, or Firm*—Brian J. Coyne

[57] ABSTRACT

A method for cleaning teeth by abrasive oral irrigation with a slurry containing a granular dentifrice composition. The dentifrice composition is gravity fed to a liquid reservoir of an oral irrigation device of the type that provides a pulsed, liquid jet stream, and forms a slurry within the reservoir. The slurry is pumped from the device and applied under pressure to teeth and gums. The composition includes a particulate baking soda having granular particles with major dimension in the range 10 to 60 microns, and a flow agent in an amount sufficient to ensure smooth and continuous gravity feed of the composition into the reservoir. A method for making the composition is described.

5 Claims, 6 Drawing Sheets

METHOD FOR CLEANING TEETH BY ABRASIVE ORAL IRRIGATION

BACKGROUND OF THE INVENTION

1. Field of the Invention

This invention relates to dentifrice compositions and methods for formulating, dispensing and using the same, and more specifically to a granular dentifrice, comprising mainly particulate baking soda, that forms a granular slurry when gravity fed into a liquid reservoir. Application of the dentifrice slurry to teeth and gums under pressure in the form of a jet stream, such as by a Water Pik®, removes stains, placque and odor from teeth and gums.

2. Background Art

It has been long known that a coating of powdered baking soda or sodium bicarbonate ($NaHCO_3$) applied to a toothbrush aids in removal of food particles, stains, and odor from teeth and gums. Powdered dentifrices, when applied directly to toothbrushes, tend to be messy and inconvenient to use, however. See, for example, U.S. Pat. No. 2,056,096 to Etter for a device for dispensing toothpowder to a toothbrush with minimum waste of powder and spillage. Thus, a variety of dentifrices, formulated in the form of stable pastes and packaged in squeezable toothpaste tubes, have largely supplanted toothpowders. Such toothpaste formulations include, among others, those described in U.S. Pat. Nos. 5,403,578, 4,980,154, and 4,522,805 to Gordon, incorporated herein, and references cited therein, and typically incorporate abrasive and polishing agents, such as calcium carbonate and sodium bicarbonate to effect the removal of dental placque, food particles and stains. Commonly, toothpaste formulations have also included whiteners as well as a fluoride compound for combining chemically into the enamel structure of the teeth so as to cause the enamel to become harder.

Tooth brushing alone, however, is usually inadequate to fully remove dental placque and to prevent dental caries and mouth odor; consequently, dental hygienists recommend daily flossing supplemented by a professional cleaning of the teeth by a dental hygienist at six month intervals. Oral irrigation devices have also been developed that provide a pulsed, liquid jet stream for cleaning where brushing and flossing cannot reach, especially around orthodontic braces, crowns and bridgework. Exemplary of such devices is the Water Pike of Teledyne Industries, Inc., of Fort Collins, Colo., as described in U.S. Pat. Nos. 4,302,186 and 4,337,040 to Cammack, et al., and 4,989,590 to Baum, et al., which disclosures are incorporated herein. Regular use of an oral irrigation device, as a supplement to regular tooth brushing and flossing, can significantly reduce inflammation, bleeding and bacteria associated with gingivitis.

Particulate sodium bicarbonate has been used as a cleaning abrasive within a jet air stream emitted under pressure through an orifice, such as for removing paint from aluminum surfaces, for instance; see, for example, U.S. Pat. Nos. 5,083,402 and 5,081,799 to Kirschner, et al.; see also, PCT/U.S. Ser. No. 90/04230. The abrasive characteristic of sodium bicarbonate has also been utilized in polishing teeth. See, for example, U.S. Pat. Nos. 3,882,638; 3,972,123; 4,174,571; 4,412,402; 4,214,871; 4,462,803; 4,482,322; 4,487,582; 4,492,575; 4,494,932; and 4,522,597. It appears, however, that the advantages inherent in directing baking soda under pressure in the form of a liquid slurry toward teeth and gums has heretofore been neither recognized nor implemented.

In sum, prior to my invention, a complete program of dental hygiene has required at least regular tooth brushing and regular flossing, supplemented by professional cleanings at six month intervals; and, in addition, for persons with braces or other dental appliances, regular cleanings by oral irrigation as well. There remains, therefore, a need for a dentifrice, and for oral hygiene apparatus for using the dentifrice, that will, through a single, convenient, daily cleaning procedure, adequately clean and whiten the teeth, and remove food particles, dental placque, and mouth odor, such that the other dental cleaning procedures will ordinarily no longer be required for maintenance of healthy, sound teeth and gums. The present invention fills that need by providing a granular, powdered dentifrice, comprising principally baking soda (sodium bicarbonate), and apparatus for dispensing the dentifrice into a liquid reservoir, to form a slurry for application to teeth and gums under pressure in the form of a liquid jet stream.

SUMMARY OF THE INVENTION

A dentifrice composition is provided comprising an admixture of particulate baking soda having granular particles with major dimension in the range of 10 to 60 microns, and a food grade flow agent. The food grade flow agent, which is preferably tricalcium phosphate, is added to the baking soda in sufficient quantity to maintain gravity feed flow of the composition under ambient conditions of use—that is, conditions of temperature 20° C. (68° F.), air pressure of one atmosphere (760) torr), and relative humidity zero to 100%. Optionally, additional ingredients are admixed into the resulting composition, including a whitener and/or a tooth placque softening agent and/or potassium nitrate.

The dentifrice composition so constituted, when added in sufficient quantity by gravity feed to a liquid reservoir, forms a slurry which, when applied under pressure by oral irrigation apparatus in the form of a jet stream, effectively removes food particles, dental placque, stains and odor from teeth and gums. Accordingly, a dentifrice dispenser is provided for use with oral irrigation apparatus that includes a liquid reservoir, such as a Water Pik®. The dispenser comprises a hopper for temporary storage of the composition. A lower portion of the hopper has a dispensing orifice. The dispenser includes means for holding the hopper over the liquid reservoir and means for opening and closing the orifice. The dentifrice composition flows through the orifice by gravity feed and into the liquid reservoir, forming a slurry therein, when, and only when, the orifice is open. The slurry is conducted under pressure from the liquid reservoir to the teeth and gums by the oral irrigation apparatus and applied thereto in the form of a jet stream.

Important objectives of the present invention therefore include the following.

It is an objective of a first aspect of the invention to provide a granular dentifrice composition which, when gravity fed into a liquid reservoir of an oral irrigation apparatus, will form a slurry within the reservoir, and said slurry, when applied under pressure in the form of a jet stream to teeth and gums, will effectively abrade and polish the teeth, remove food particles, dental placque and stains from the teeth, irrigate the gums, and eliminate mouth odor—all without creating any injury to the teeth or gums if properly used.

An additional objective of the first aspect of the invention is to provide such a dentifrice composition that includes, as its principal component, particulate baking soda comprised of particles having major dimension in the range 10 to 60 microns, the baking soda being admixed with a food grade flow agent in sufficient quantity to ensure smooth gravity feed flow of the composition under typical conditions of use—namely, ambient conditions that include 20° C. (68° F.), one atmosphere pressure, and zero to 100% relative humidity.

In a second aspect of the invention, it is a further object of the invention to provide a dentifrice dispenser for creating a slurry within a liquid reservoir of an oral irrigation apparatus by gravity feed of the dentifrice composition into the liquid reservoir.

A still further object of the second aspect of the invention is to provide such a dentifrice dispenser in a first embodiment that is mountable directly upon the liquid reservoir of an oral irrigation apparatus.

Another object of the second aspect of the invention is to provide such a dentifrice dispenser in a second embodiment that is wall mountable above the liquid reservoir of an oral irrigation apparatus.

In a third aspect of the invention, it is an object of the invention to provide a method for formulating a granular dentifrice composition, adapted for smooth gravity feed into a liquid reservoir of an oral irrigation apparatus to form a slurry therein for effective oral irrigation and cleaning of teeth and gums when applied thereto in the form of a pressurized, jet stream, under ambient conditions that include 20° C. (68°0 F.), one atmosphere pressure, and zero to 100% relative humidity.

DETAILED DESCRIPTION OF THE PREFERRED EMBODIMENT

Figure 1:
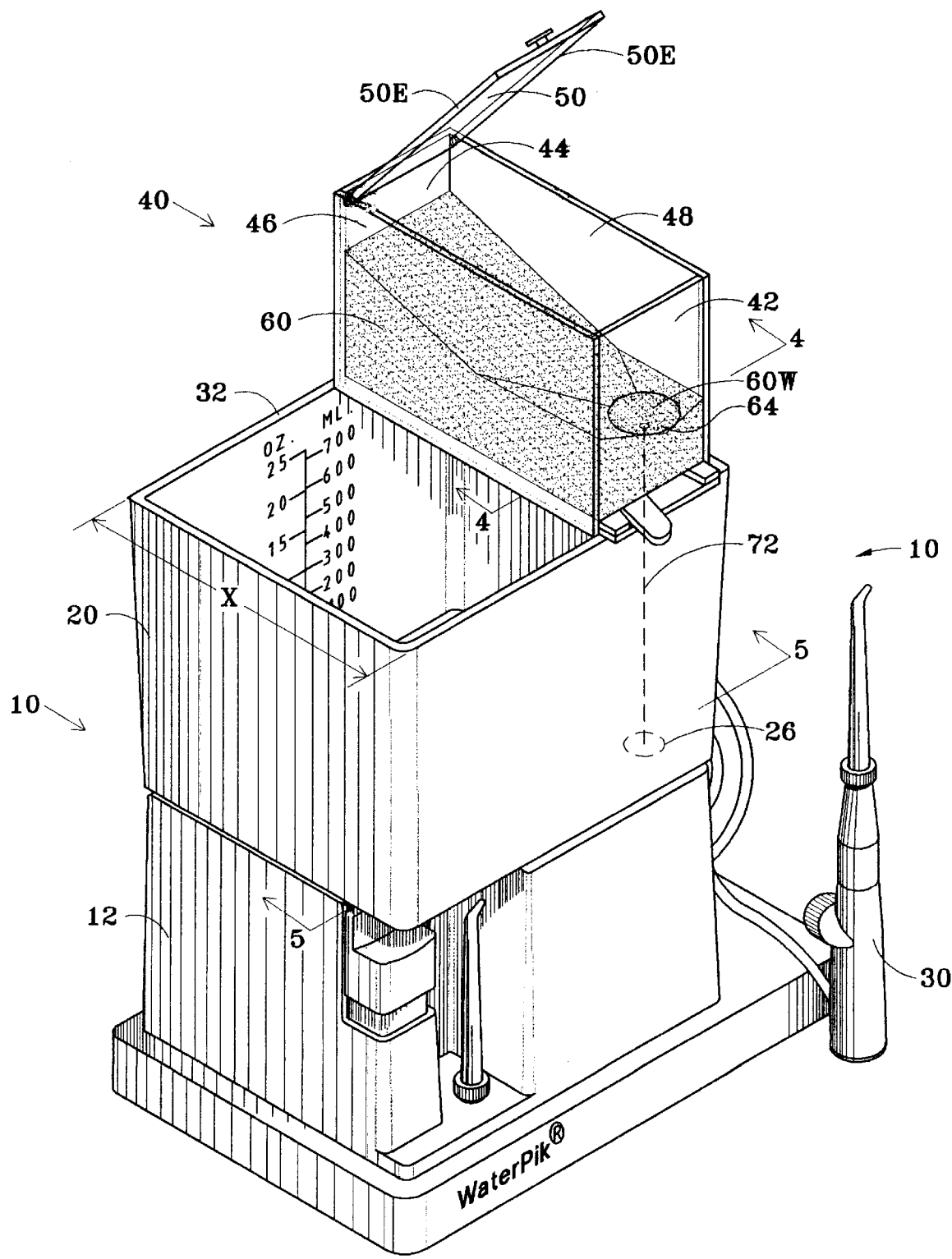
FIG. 1 is frontal perspective view of my dentifrice dispenser mounted directly on a Water Pik® oral irrigation apparatus, prior to adding my dentifrice composition thereto, and with the dispenser orifice open.

To formulate a preferred embodiment of the dentifrice composition of the present invention, particulate baking soda, i.e., sodium bicarbonate U.S.P. having chemical formula $NaHCO_3$, is passed through one or more screens to select only those particles thereof having major dimension in the range 10 to 60 microns. For example, suitably screened particulate baking soda may be prepared by passing particulate baking soda through a screen having pores that pass particles with major dimension 45 microns or less. The screened particulate baking soda is thereafter admixed with a dry, particulate food grade flow agent to form a first mix. The amount of food grade flow agent admixed into the first mix should be in sufficient quantity to ensure that the first mix will gravity feed smoothly and uniformly through a circular orifice of a dentifrice dispenser (described below) under typical conditions of use, wherein the orifice has diameter in the range 0.5 to 4 mm, and preferably has diameter 2 mm. It will be understood that, although the dentifrice composition may be used under widely varying conditions, typical conditions of use are here defined to include at least the following: 20° C. (68° F.), one atmosphere (760 torr) pressure, and zero to 100% relative humidity. Preferably, the food grade flow agent is tricalcium phosphate, in which case the tricalcium phosphate is preferably admixed into the first mix to 0.5 to 5.0% by weight final concentration, or, more preferably, to 0.5 to 2.0% by weight final concentration. The tricalcium phosphate is preferably FCC or C.P. grade. Optionally, additional components may thereafter be added to the first mix. For instance, a tooth whitener may be admixed with the first mix to form a second mix. Potassium nitrate may also be advantageously admixed into the second mix to form a third mix, preferably to 0.2 to 0.4% by weight final concentration. Other components well known to those skilled in the art of formulating dentifrices can also be incorporated into the dentifrice composition—e.g., a fluoride compound for hardening tooth enamel, sweeteners, etc.

Figure 5:
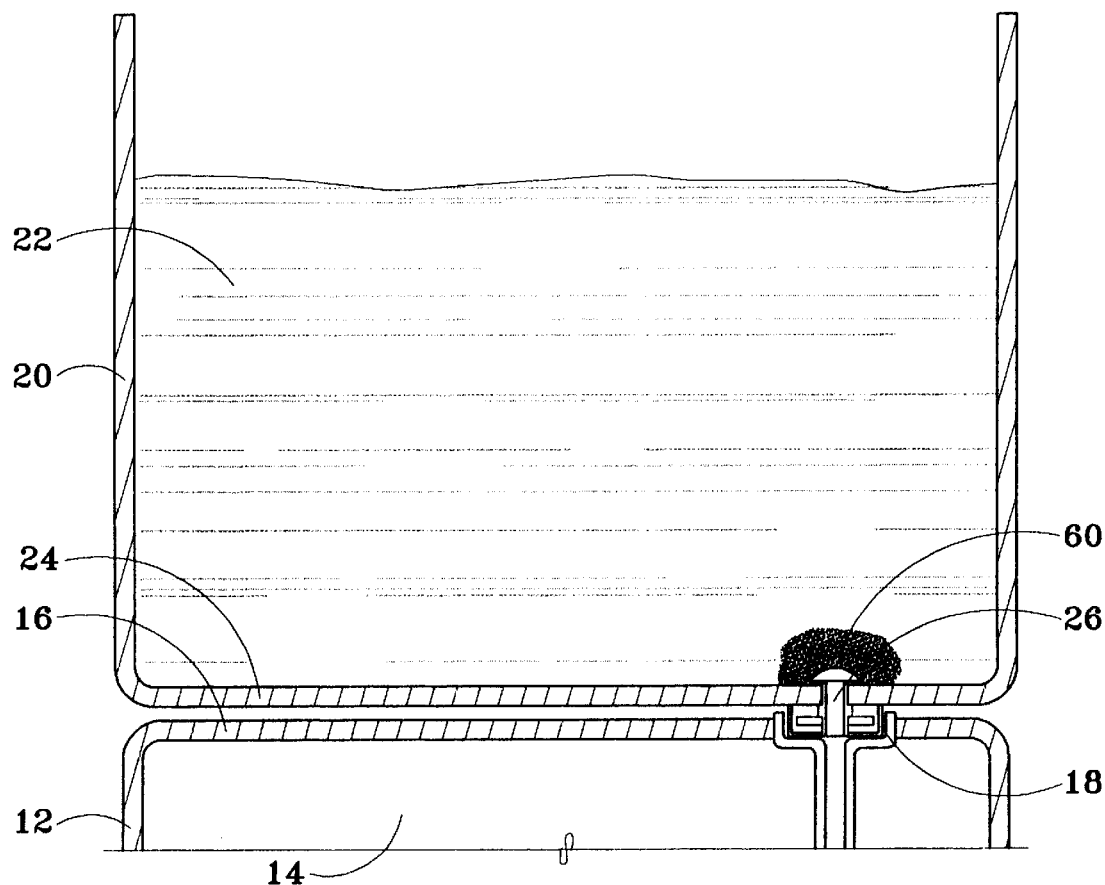
FIG. 5 is a cross-sectional view taken along line 5—5 of FIG. 1 showing a slurry of my dentifrice composition having formed within the water reservoir of the Water Pik®.

Referring now to FIGS. 1 and 5, an oral irrigation apparatus 10 is depicted and, more specifically, a Water Pik® oral irrigation apparatus manufactured by Teledyne Industries of Fort Collins, Colo. The apparatus 10, which is prior art and forms no part of the present invention, includes a housing 12 that defines a cavity 14. The housing 12 includes a horizontal top wall 16 that is apertured to form an inlet port 18 for receiving liquid by gravity feed from an overlying, invertable cover 20. The cover 20, as depicted in FIGS. 1 and 5 is shown in an inverted position, in which position it serves to contain a liquid reservoir 22, as shown in FIG. 5. The liquid reservoir 22 may be water or any liquid suitable for irrigating teeth and gums, such as a mouthwash or anti-bacterial rinse. Incorporated into the bottom wall 24 of the cover 12 is an outlet valve 26, depicted in FIG. 6 and shown in phantom outline in FIG. 1, that directly overlies the inlet port 18 when the cover 20 rests upon the top wall 16; when in such overlying position, the outlet valve 26 is open, but the valve 26 automatically closes whenever the cover 20 is lifted off the top wall 16. Housed within the cavity 14 is a pump (not shown) that, when energized, pumps liquid, received from the liquid reservoir 22, under controllable pressure out through a hand-held device 30 for application to teeth and gums in the form of a pulsed, jet stream.

A first embodiment of the dentifrice dispenser of the present invention, denoted generally by the numeral 40, is shown in FIG. 1 resting on an upper edge 32 of the inverted cover 20. The dispenser 40 includes vertical, oppositely-disposed, rectangular front and rear walls 42, 44, joined by vertical, oppositely-disposed, left and right side walls 46, 48, respectively. A rectangular lid 50 is pivotally attached to upper, rear portions of the side walls 46, 48—for example, by a pair of oppositely-directed nibs (not shown) projecting from inside surfaces of said walls 46, 48 and inserted into recesses (not shown) within side edges 50E of the lid 50. The lid 50 is movable between a vertical, open position, for adding dentifrice composition 80 (indiciated by stippling) to the dispenser, and a horizontal, closed, sealing position in contact with upper edges of the front 42, rear 44, and side 46, 48 walls, when dispensing dentifrice 80 therefrom. The front-to-rear length of the side walls 46, 48 and of the lid 50 is substantially equal to the front-to-rear length X of the upper edge 32 of the inverted cover 20.

Figure 2:
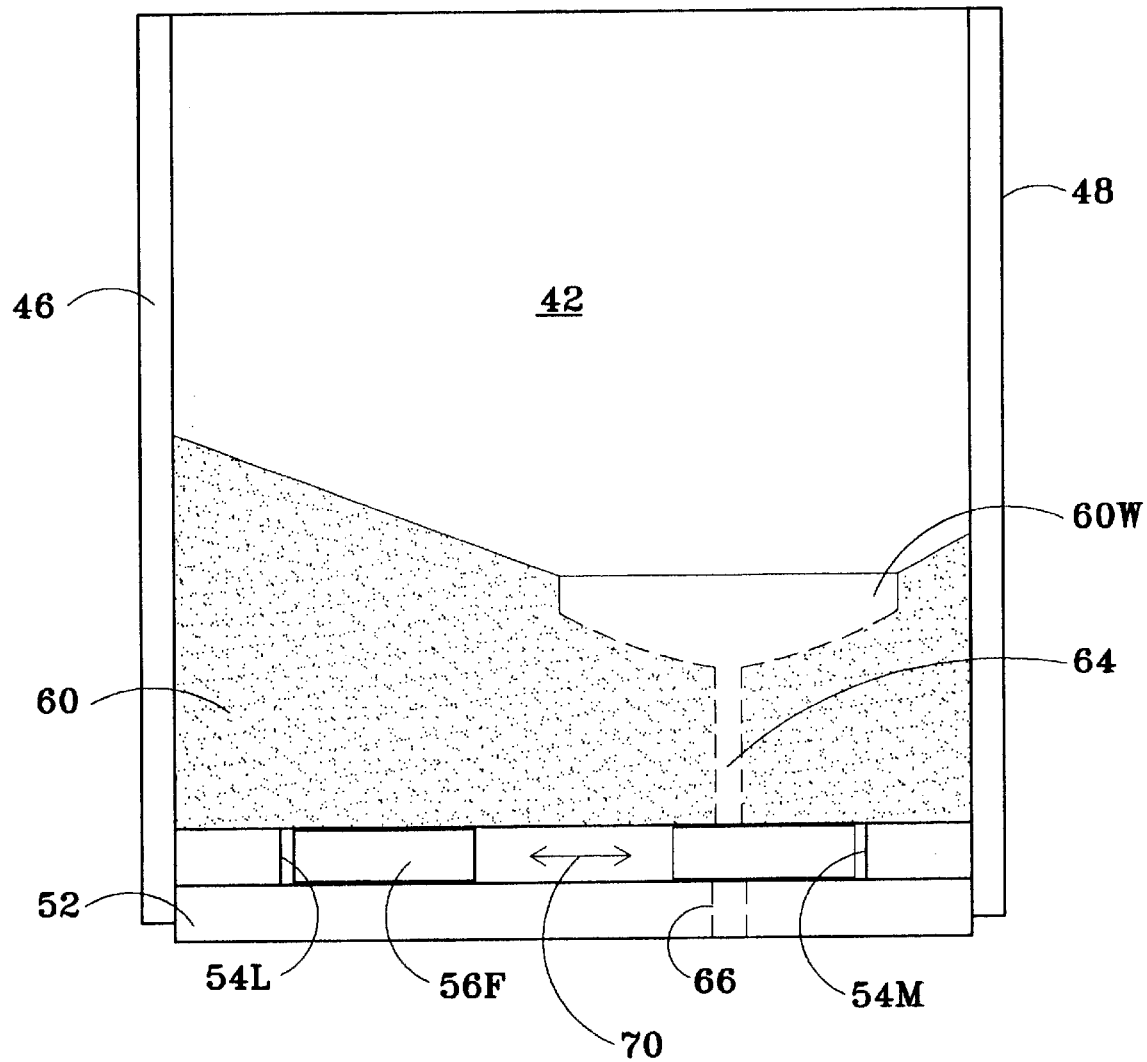
FIG. 2 is a front elevational view thereof.
Figure 3:
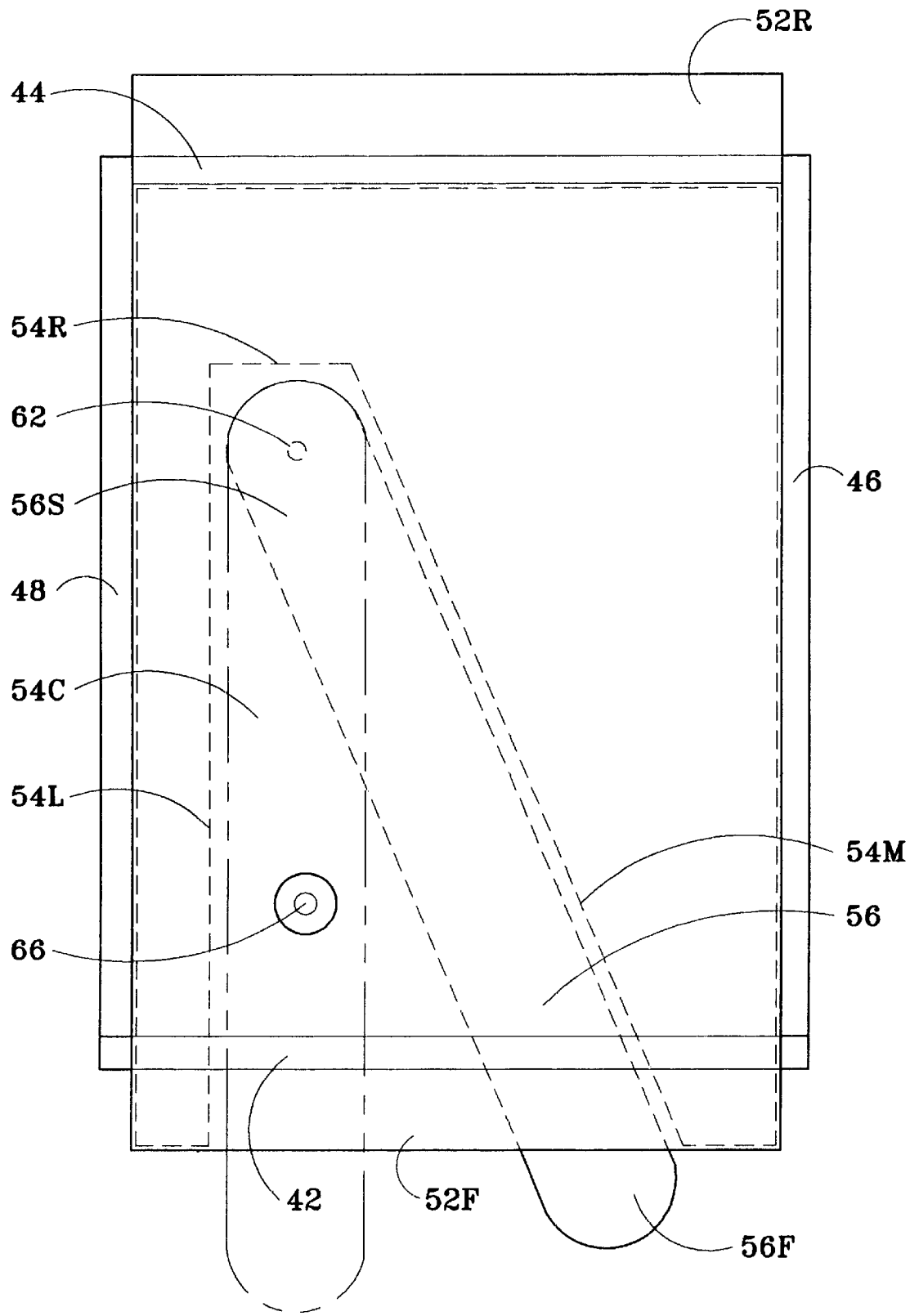
FIG. 3 is a bottom view thereof.

The dispenser 40 further includes a flat, rectangular, base plate 52 interposed between, and joined to, apposed lower surfaces of the left and right side walls 46, 48. The base plate 52 extends from front to rear somewhat more than length X, thereby forming a front lip portion 52F and a rear lip portion 52R that extend forwardly and rearwardly of the front and rear walls, 42, 44, respectively. As may be seen in FIG. 3, in overlying contact with the base plate is a guide plate 54, N-shaped in bottom plan view, that extends a distance X from front to rear. The base plate 54 has a notched cutout 54C defined by a longitudinally-directed, straight left edge 54L and an oblique right edge 54M joined by a laterally-disposed rear edge 54R. In overlying contact with the guide plate 54, and extending upwardly therefrom to partially fill a lower portion of the space defined by the front 42, rear 44 and side 46, 48 walls, is a dentrifice support block 60. A flat, longitudinally-elongated closure member 56 is interposed between the support block 60 and the bottom panel 52, and is disposed within the cutout 54C. The closure member 56 has a first end 54S pivotally attached to a lower portion of the support block 60 for rotation around pivot point 62, and an opposite free end 54F that extends forwardly from the dispenser 40. The support block 60 has recessed well 60W that communicates with a downwardly-directed, first dispensing orifice 64 that colinearly overlies a second, downwardly-directed dispensing orifice 66 in the bottom panel 52, said second orifice 66 being disposed directly underneath the notched cutout 54C and near the left edge 54L thereof. As the arrow 70 in FIG. 2 indicates, the closure member 56 is movable from a first, orifice-unconvered, open position, as shown in solid lines in FIGS. 2–4, to a second, closed, orifice-covered position, as shown in phantom outline in FIG. 2. The block 60 has obliquely canted upper surfaces to promote gravity feed of the dentifrice composition 80 through orifices 64, 66. The front and rear walls 42, 46, the side walls 46, 48, the lid, 50, the bottom plate 52, the guide plate 54, and the block 60, are all preferably made of transparent, rigid plastic.

Figure 4:
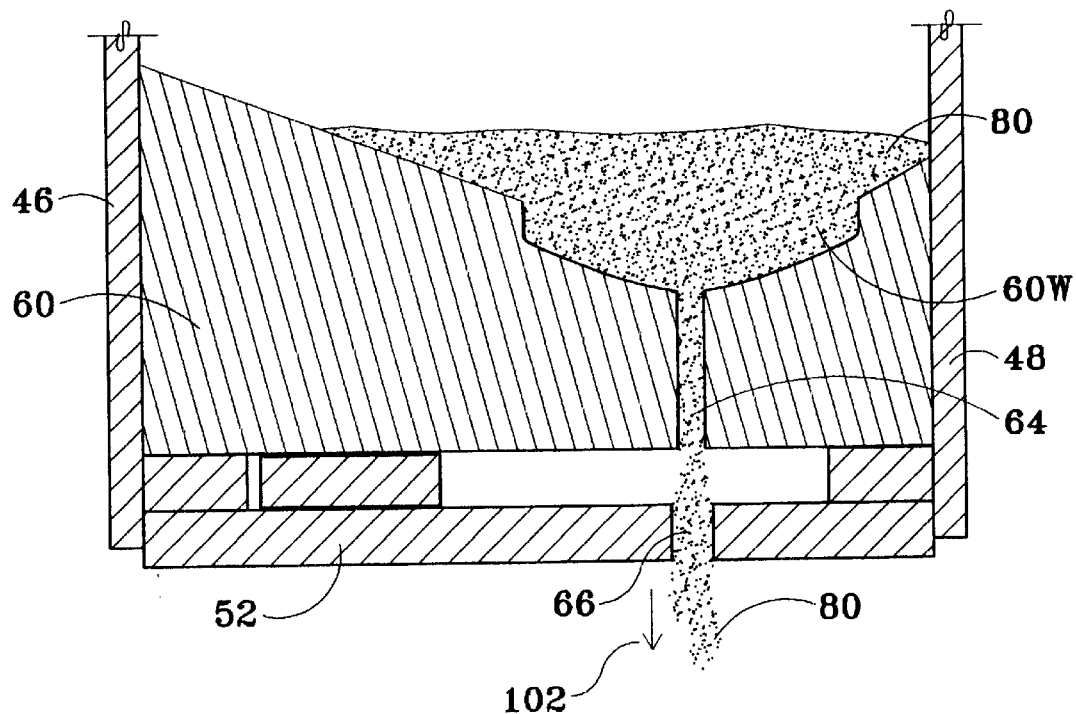
FIG. 4 is a cross-sectional view taken along line 4—4 of FIG. 1, after adding my dentifrice composition thereto.

In use, a suitable liquid, such as water, mouthwash, or an anti-bacterial rinse, is introduced into the inverted cover 20 to form a liquid reservoir 22 therein. The first embodiment of the dispenser 40, as heretofore described, is then rested on edge 32 of the inverted cover 20, such that the well 60W and the first dispensing orifice 64 therein directly and colinearly overlie the oulet valve 26, as indicated in FIG. 1 by the dashed vertical line 72. With the lid 50 raised, and the closure member 56 in a closed position, a quantity of the above-described granular dentifrice composition 80 is placed into the well 60W and onto the dentifrice support block 60, as shown in FIGS. 4 and 5. The lid 50 is then closed, and the closure member 56 is moved to an open position, thereby permitting the dentifrice composition 80 to fall through the first and second dispensing orifices 64, 66, as indicated by arrow 102 in FIG. 4, and to collect on the interior bottom 24 of the inverted cover 20 over, and in the vicinity of, the outlet valve 26, wherein the dentifrice composition and the liquid reservoir cooperate to form a slurry. The hand-held device 30 is grasped and directed toward teeth and gums, and the pump is then energized, thereby drawing the slurry out of the reservoir 22, through the hand-held device 30, and applying the slurry to the teeth and gums in the form of a jet stream.

Figure 6:
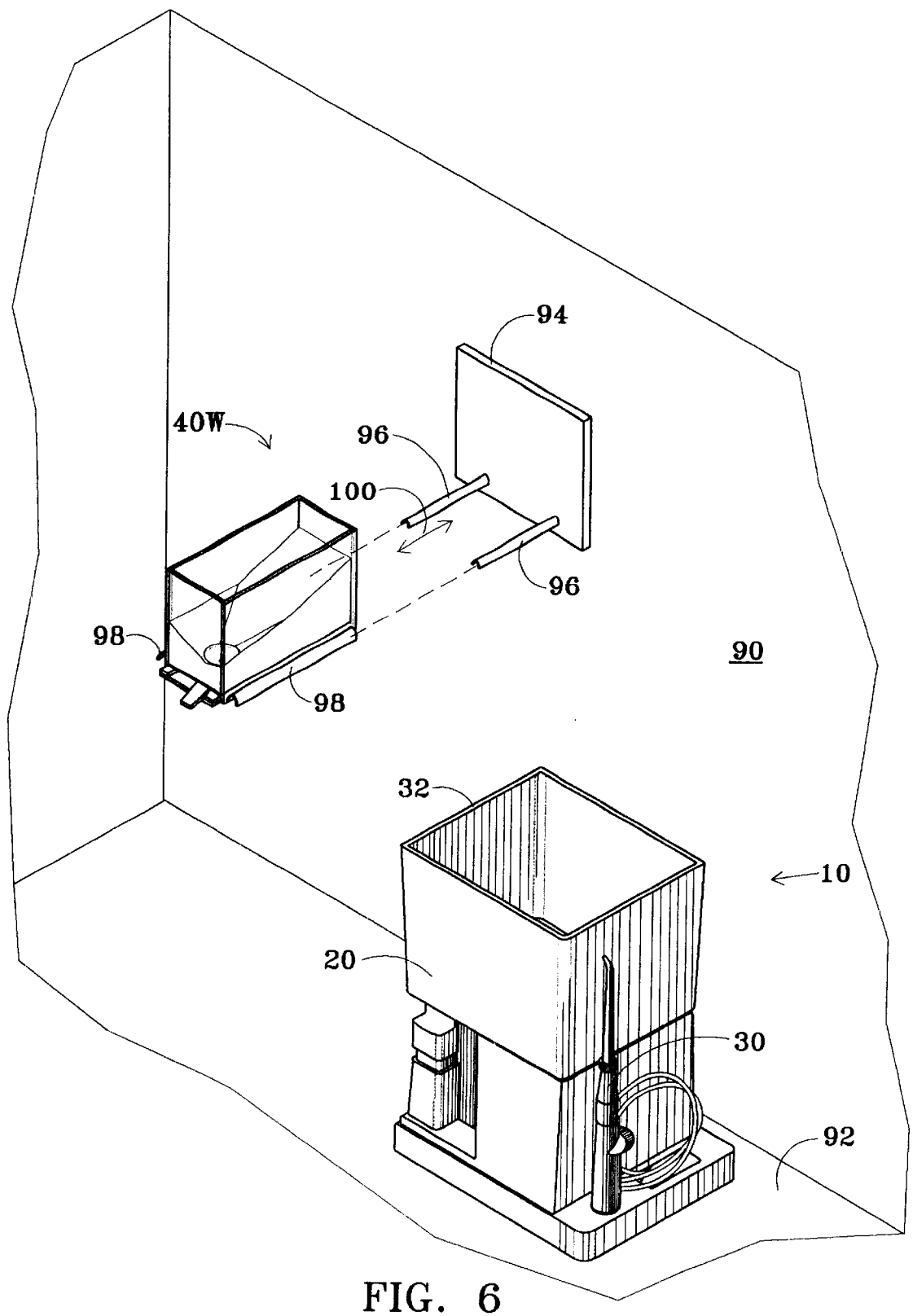
FIG. 6 shows a wall mountable version of my dentifrice dispenser.

Referring now to FIG. 6, a second, wall mountable embodiment of the dispenser is shown, denoted generally by the numeral 40W, mounted on a wall 90 directly over the inverted cover 20 of an oral irrigation apparatus 10 resting on a countertop 92. This version is identical to the first embodiment 40, except that it further comprises a backing plate 94 adapted for mounting on a wall 92, and a first pair of spaced-apart, horizontal rails 96 that extend forwardly from the backing plate 94. A second pair of spaced-apart, horizontal rails 98 are attached to a lower portion of the dispenser 40W, such as to the side walls 46, 48 thereof, for sliding engagement with the first pair of rails 96, as indicated by arrow 100 in FIG. 6. The first and second pairs of rails 96, 98 have means (not shown) for locking and unlocking the dispenser in fixed relation to the mounting block 94 so that the dispenser may be easily attached to, and removed from the mounting block 94.

Various changes and modifications will become obvious to those skilled in the art. It is the intent that these changes and modifications are to be encompassed within the spirit of the appended claims and that the invention described herein and shown in the accompanying drawings is illustrative only and not intended to limit the scope of the invention.

I claim:

1. A method for cleaning teeth, comprising the steps of:
   (a) adding by gravity feed a granular dentifrice composition to a liquid reservoir to form a slurry therein;
   (b) pumping said slurry from said liquid reservoir toward the teeth; and
   (c) applying said slurry under pressure in the form of a jet stream to the teeth;
   wherein said composition includes a particulate baking soda having granular particles with major dimension in the range 10 to 60 microns, and a food grade flow agent in an amount sufficient to maintain gravity feed flow of the composition under ambient conditions that include temperature of 20 degrees C. (68 degrees F.), air pressure of one atmosphere (760 torr), and relative humidity of up to 100%.

2. The method of claim 1, wherein the slurry is formed within an oral irritation device that provides a pulsed, liquid let stream, and the slurry is applied under pressure in a jet stream to the teeth by said device.

3. A method for making a granular dentifrice composition, comprising the steps of:
   (a) screening granular baking soda through a screen having 45 micron pores, and retaining the portion thereof that passes through said screen;
   (b) admixing said retained portion of the baking soda of step (a) with a food grade flow agent to form a first mix, said food grade flow agent being in a sufficient amount to maintain gravity feed flow of the composition under ambient conditions that include temperature of 20 degrees C. (68 degrees F.), air pressure of one atmosphere (760 torr), and relative humidity of up to 100%.

4. The method of claim 3, wherein the flow agent is 0.5 to 5.0% by weight tricalcium phosphate in the first mix.

5. The method of claim 4, further comprising admixing potassium nitrate with the first mix to form a second mix comprising 0.2 to 0.4% potassium nitrate by weight in said second mix.

* * * * *